United States Patent [19]

Berthold et al.

[11] Patent Number: 4,863,690
[45] Date of Patent: Sep. 5, 1989

[54] MEASURING INSTRUMENT FOR BIOLUMINESCENCE AND CHEMILUMNESCENCE OR TURBIDIMETRY

[75] Inventors: Fritz Berthold, Pforzheim; Willy Lohr, Wildbad, both of Fed. Rep. of Germany

[73] Assignee: Laboratorium Prof. Dr. Rudolf Berthold, Wilbad, Fed. Rep. of Germany

[21] Appl. No.: 52,291

[22] Filed: May 21, 1987

[30] Foreign Application Priority Data

Jul. 12, 1986 [DE] Fed. Rep. of Germany ....... 3623601

[51] Int. Cl.$^4$ .................. G01N 21/76; G01N 35/04
[52] U.S. Cl. ......................................... 422/52; 422/65; 422/104
[58] Field of Search ............... 422/52, 58, 65, 71, 422/104; D24/32; 211/74

[56] References Cited

U.S. PATENT DOCUMENTS

| | | | |
|---|---|---|---|
| 3,587,676 | 6/1971 | Oehlin et al. | 422/65 |
| 3,713,771 | 1/1973 | Taylor et al. | 211/74 |
| 3,898,457 | 8/1975 | Packard et al. | 422/71 |
| 4,076,420 | 2/1978 | De Maeyer et al. | 356/338 |
| 4,634,575 | 1/1987 | Kawakami et al. | 422/104 |
| 4,699,767 | 10/1987 | Aihara | 422/65 |

Primary Examiner—Michael S. Marcus

[57] ABSTRACT

A measuring instrument for bioluminescence and chemiluminescence has coupled holders that can slide on a horizontal locating surface with specimen pans, which are fed successively to a light entry port (point of measurement) which is shielded outwardly in light-tight fashion. The holders are fitted with a side window and the point of measurement is placed at the level of these windows opposite thereto.

Among other advantages, the specimen pans need no longer be removed from their holders in order to carry out the measurement at the point of measurement, but can remain therein. The mechanical driving and sliding mechanisms for this vertical lift needed heretofore can thus be dispensed with.

15 Claims, 7 Drawing Sheets

MEASURING INSTRUMENT FOR BIOLUMINESCENCE AND CHEMILUMNESCENCE OR TURBIDIMETRY

BACKGROUND OF THE INVENTION

The invention relates to a measuring instrument for measuring bioluminescence and chemiluminescence.

Bioluminescence and chemiluminescence have come into widespread use in medical applications for the investigation of a very wide variety of specimens. One reason which has contributed to this is the fact that it is not necessary to work with radioactive materials, whose manipulation and storage is troublesome and expensive for many users.

In bioluminescence and chemiluminescence, a special substance (activator) is added to the specimen to be investigated, and in particular injected thereinto, after the addition of which a relatively rapid reaction ensues which is associated with the emission of light. This light emission can be detected by a suitable optical detector, e.g., a photomultiplier, and converted into an electrical signal, after which it is possible, from the intensity of the light signal and the time lapse, to draw conlusions as to the nature of the specimen and, in particular, the presence of specific substances.

An essential aspect of this method is that, because of the rapidly occurring light reaction, the activator can only be injected if the specimen has already reached the point of measurement in front of the light entry port of the optical detector.

It is obvious that the point of measurement, i.e. the area in front of the light-sensitive opening of the optical detector, must be completely shielded from stray light, at least during the measuring procedure in order to achieve reliable results of measurement. The complete sealing of the point of measurement requires a certain technical complexity in customary commercial instruments as exemplfied in applicant's Published German patent application No. 3,239,866, which relates to a dimmable measuring station for a photometer.

Another requirement imposed on such measuring instruments lies in the fact that they must be able to measure the largest number of specimens as efficiently, i.e. as automatically, as possible, that is to say, that the specimen pan with the substance to be measured is brought to the point of measurement, the activator(s) is/are injected thereinto, and the specimen pan remains at the point of measurement until the light reaction has decayed.

In the above-cited Published German patent application No. 3,239,866 and in applicant's commercially available instrument ("Autobiolumat LB 950"), an attempt is made at the same time to satisfy these requirements by introducing a large number of specimen pans in holders which can be coupled together and by moving them past the point of measurement therebeneath. Here, the point of measurement incorporates a housing block with a cylindrical interior, which is connected to the light entry port of the optical detector. The holders for the specimen pans are open at the bottom so that, by means of a piston mechanism, one specimen pan at a time can be pushed from below into the housing block, and thus to the point of measurement.

Thus, for the measuring process, each specimen pan is pushed out of its own holder by a vertical lift and is returned thereto after the measurement has been completed, after which the chain of holders coupled together is moved further by one link and this measuring process is repeated.

Admittedly, this prior art approach produces a certain automation effect owing to the fact that the holders for the specimen pans are coupled in chain-like fashion but, on the one hand, the means for lifting the specimen pans vertically to the point of measurement and, on the other, the means for light-tight shielding of the point of measurement when a specimen pan is introduced thereinto call for a high mechanical precision, and they are therefore relatively expensive. The time required for the lifting motions must be added to the time of the actual measurement, and thus constitutes dead time, which deleteriously affects the efficiency of measurement of many specimens.

SUMMARY OF THE INVENTION

The object of the invention consists in modifying the measuring instrument of this type in such a way as to achieve a more rapid sequential measurement and a simplification of the construction of the apparatus.

This object is achieved by the characterizing clause of claim 1.

Therefore, the basic concept of the invention is seen in the fact that the specimen pans need no longer be removed from their holders for measurement at the point of measurement, but can remain therein. This means, in the final analysis, that the vertical lifting motion for guiding the specimen pans out of their holders and into the point of measurement can be dispensed with. As a result, all mechanical drive and sliding devices for this vertical lift are eliminated.

The problem of the light-tight shielding is solved, in accordance with one embodiment of the invention, in that a cover plate seals off in light-tight fashion the entire surface locating the holders, along with the specimen pans, so that, at least during the measurement, a total dimming of the entire volume around the specimen pans is achieved.

In addition, a horizontally extending channel is provided for the specimen holders which, by means of a shadow screen, prevents damage to the optical detector when the cover plate is open.

A problem which constantly arises in taking a large series measurement on a laboratory scale is the faultless identification and allocation of the specimen pans, i.e., in maintaining the sequence of specimen pans in the holders throughout the measuring process. Here, the manual adjustment of the individual specimen containers in their own holders and their removal, which must be carried out after the measurement, requires increased attention on the part of the laboratory workers, since an interchange of the sequence or a confusion of the specimens may lead to serious misjudgments of the laboratory findings concerning the patient involved and, in extreme cases, therapeutic procedures may be initiated or omitted that would be inadequate or urgently needed.

Heretofore, rationalization of this operating step (insertion and subsequent removal of the specimen pans from the containers) was not possible in the art (Published German patent application No. 3,239,866) since, in the sense of con-veyor technology, the removal of the test tubes from their holders in order to convey them to the point of measurement constitutes a temporary separation technology, and this naturally also affects the procedure for loading and unloading the holders with the specimen pans.

This mandatory separation is dispensed with by the scheme incorporating the invention, in which the specimen pans can remain in "their own" holders even at the point of measurement, and thus the relative position of successive specimen pans, at least in the vertical direction, remains unchanged from the time of loading to the time of unloading.

In accordance with another specific embodiment of the invention, this opens the possibility of combining the specimen pans in groups, so that they can be loaded as a group into their own holders and can again be removed therefrom as a group after the measurement has been completed. This means, on the one hand, a reduction in the actions required for loading and unloading, thereby promoting the degree of automation of the measuring instrument and, in addition, it also produces an increased security with respect to interchanges in the sequence, since the combining of several specimen pans into groups prevents interchange within one group, and the interchange of groups between each other is much less likely.

Advantageously, the creation of suitable combinations of specimen pans can also be used to assign a particular common parameter to each group of specimen pans, for example, the name of one patient with different specimens, or also one particular specimen substance for different patients.

If desired, these coupled specimen pans can either be integrally formed, so that they cannot be detached from each other, or they can be coupled together by means of a flexible coupling element, so that the connection becomes detachable and the specimen pans can also be used in different ways, if required.

According to another specific embodiment, further simplification in the area of the loading and unloading stations of the measuring instrument can be achieved if, in accordance with another specific embodiment, means are provided which, at least in the area of the loading and unloading stations, align one group of specimen pans linearly along their length. This can be done either by resilient tie bars between the specimen pans or by a straight guide section in the locating surface of the measuring instrument (or both), so that at any one time a single group of specimen pan is aligned linearly, permitting a definite loading and unloading of the specimen pan.

In accordance with specific embodiments, one can, through other expedients, apply markers or small labels to the specimen pans to give appropriate information about the contents of the specimen or other parameters (so-called bar codes). Here again, there is the advantage that by combining several specimen pans into one group of specimen pans, and thereby cancelling the rotational symmetry of the specimen pan, a definite position of these markers can be achieved, especially at the loading and unloading stations and, in particular, that an orientation of these bar code labels, once it has been chosen, e.g., facing the operator, will again be taken up at the unloading station. Finally, another embodiment of the invention provides that the holders each have a second opening essentially diametrically opposite to the first opening. Unlike measurements of bioluminescence and chemiluminescence, in which the light activity comes from the specimen itself, it is also possible with this expedient to perform turbidimetry, i.e., measurements which call for a light beam emitted from the outside and passing through the specimen, and whose loss in intensity by absorption effects in the specimen ultimately represents the quantity measured.

Therefore, the basic idea of the invention to allow the specimen pans to remain in their own holders, even at the point of measurement, makes it possible to carry out a large number of additional steps which promote the efficiency and reliability of the measuring process.

Further embodiments will become apparent from the other subclaims.

BRIEF DESCRIPTION OF THE DRAWINGS

One embodiment of the measuring station will now be discussed with reference to the accompanying drawings, in which.

Figure 1:
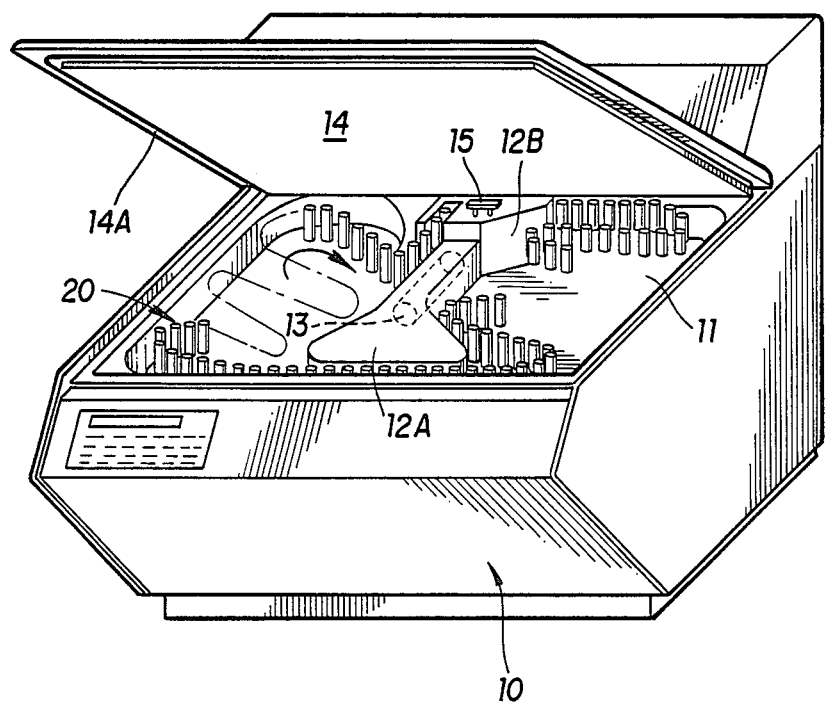
FIG. 1 is an overall perspective view of the measuring instrument, with the cover plate open.

The measuring instrument 10 has a horizontal locating surface 11 for specimen chain 20 made up of holders and specimen pans, as will be explained in detail hereinafter. Three star-shaped wheels 16, 17 and 18 are mounted in this locating surface 11, with their axes perpendicular thereto and driven together by a motor (not shown) in such a way that their rotational speed and their sense of direction are so adjusted to each other that, together, they bring about the transport of the specimen chain 20 on the locating surface 11. The bearing axis of the central star-shaped wheel 17 lies in a common surface with the longitudinal axis of a optical detector, for example, a photomultiplier 13, whose light entry port forms the measuring station 19A of the measuring instrument. Consequently, the specimen chain 20, driven by star-shaped wheels 16, 17 and 18, is moved toward the arrow through the measuring station 19A, i.e., past the light entry port of photomultiplier 13. An injector 15 is mounted to slide vertically (FIG. 7) above the particular element of the specimen chain 20 located in the measuring station 19A, the indicator liquid being injected by the injector 15 into the sample vessel concerned at the start of the luminescence reaction. The resulting luminescence is recorded by the photomultiplier 13 and is converted in a known manner into an electrical pulse, whose shape then permits conclusions to be drawn as to the nature and composition of the specimen in the specimen pan after these signals have been evaluated.

Lateral guide elements 12A . . . 12D are provided for the proper guidance of the specimen chain 20, which elements will be explained in greater detail hereinafter. They consist of plastic parts fastened to the locating surface 11 and dividing the latter.

In the area of the measuring station 19A there is a guide element 12B, which has on its rear end a semi-circular notch into which projects the central star-shaped wheel 17. On both sides of this semi-circular notch are curved extensions which partially surround the two outermost star-shaped wheels 16 and 18.

Another guide element 12C is located on the rear edge and on the two side edges of the locating surface 11, its part opposite the guide element 12B being shaped such that it likewise surrounds partially the three star-shaped wheels 16, 17 and 18 circumferentially. In the area of entrance into measuring station 19A, i.e., directly in front of the first star-shaped wheel 16, are the two guide elements 12B and 12C, with their vertical side faces opposite each other. An identification station 19C for the specimen chain 20, which contains a laser scanner, is arranged in this extension of the guide element 12C. Thus, in their opposing parts the two guide elements 12B and 12C, including the three start-shaped wheels 16, 17 and 18, define a first guide channel for the specimen chain 20, through which they are moved successively past the measuring station 19A.

The front end of the optical detector 13 extends into the front part of the guide element 12B, which optical detector 13 is terminated by a window 13A (FIG. 7), thereby establishing the optical connection between the specimen chain 20 in the first guide channel, on one side, and the optical detector 13, on the other.

The rear part of the optical detector 13 is covered by another guide element 12A, which is shaped substantially like a T, said guide element 12A having a straight edge on the side opposite the measuring station 19A. This straight edge of the guide element 12A lies opposite the straight edge of another guide element 12D, which is fastened to the front edge area of the locating surface 11. Thus, a second guide channel is created in the space between these two guide elements 12A and 12B, and the specimen chain is aligned linearly in this guide channel. This guide channel serves as loading and unloading station 19B, into which the specimens are inserted or, after the measurement, are removed.

The remaining space in the locating surface 11, which is not covered by the guide elements 12A . . . 12D, serves to locate the specimen chain ahead of the measuring station 19A (left half) or to locate the specimens measured in the measuring station 19A (right half), before they again move to the unloading station 19B.

Another function of the guide elements 12B and 12C, in conjunction with the blades 16A, 17A and 18A, is to protect the measuring station 19A, i.e. especially the extremely light-sensitive entrance opening of the optical detector 13, from the incidence of unwanted light entering through the exit and entrance opening of the guide channel, when the cover plate 14 is opened.

The cover plate 14 has a circumferential rubber seal 14A, with which it can be fastened to the outer edge of the measuring instrument 10. During operation of the measuring instrument, i.e., when performing measurements in the measuring station 19A, the cover plate 14 is folded downward, so that the volume enclosed by the locating surface 11, the surfaces of the guide elements 12A . . . 12D and the lower side of the cover plate 14, in which the specimen chain is located, is sealed off in absolutely light-tight fashion, and thus an essential prerequisite is met for carrying out correct measurements in the measuring station 19A.

A measuring cycle runs as follows:

First, the specimen chain 20 is fitted with specimen pans, which contain the particular specimens to be examined. After this has been done, the cover plate 19 is closed and thus the entire locating volume defined above is sealed off in light-tight fashion. Now, star-shaped wheels 16, 17 and 18 project with their radially placed blades into the interstices of the specimen chain and convey them further under clock control in such a way that, one after the other, they pass through the measuring station 19A, where the tip of the injector 15 is lowered into the specimen pan concerned, the measurement is carried out, and the chain moves on by one position. Aside from driving the specimen chain, the blades 16A, 17A and 18A also serve to create a screening effect on the specimen pan, which is just at the measuring station 19A, with respect to the adjacent specimen pans, so that residual or stray radiation from the adjacent specimen pans cannot reach the optical detector 13.

With the above-described arrangement, it is essential that the optical detector 13 be likewise placed on the locating surface 11, and that therefore its light entry port be located on the level of the specimen chain 20 so that, in contradistinction to the prior art, the specimen pans need not be removed from the specimen chain in order to be measured. The measuring station 19A is an integral part of the guide element 12B.

Figure 2:
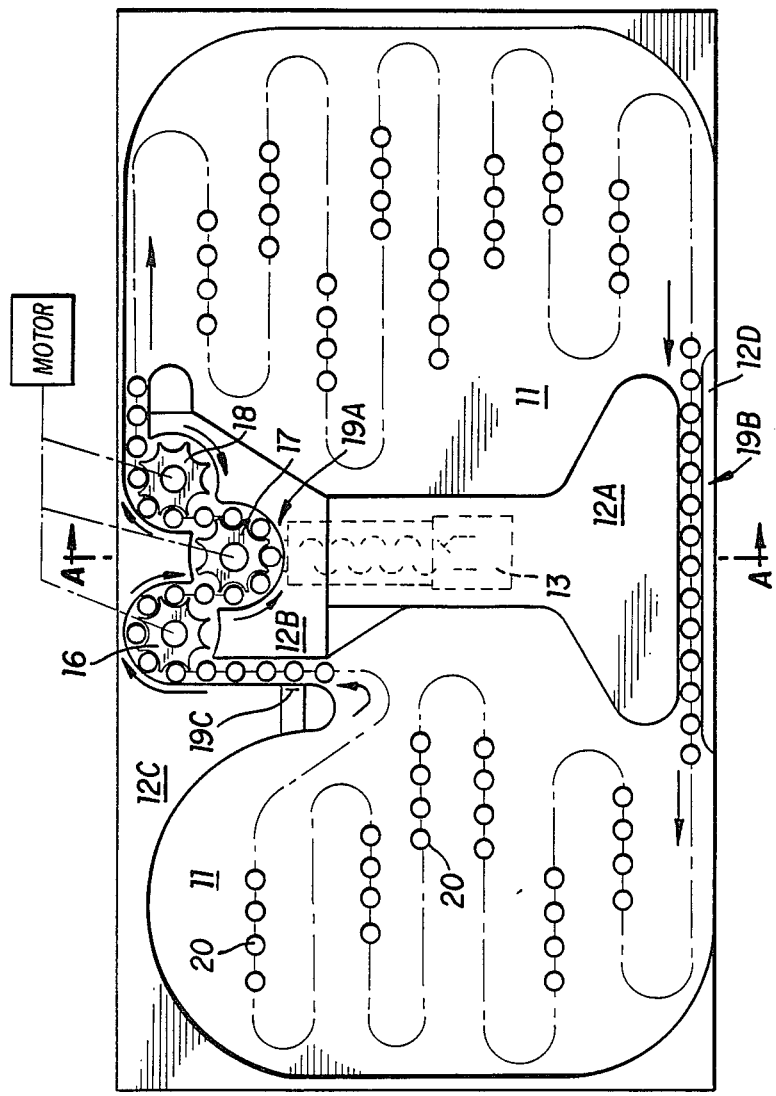
FIG. 2 is a plan view of the locating surface for the specimen chain, with the cover plate removed.
Figure 3:
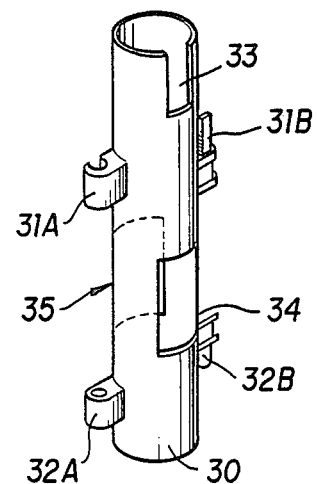
FIG. 3 is a perspective view of a specimen pan holder for the specimen chain.

In order to achieve this, the invention makes use of a special construction of the specimen chain 20, which will be explained in the following section:

A specimen pan holder 30 shown in FIG. 3 consists of a small cylindrical plastic tube into which the specimen pan can be inserted from above. These holders have coupling elements on opposing sides, by means of which any desired number of holders 30 can be connected together to pivot about a vertical axis so that, after insertion of the specimen pans, the specimen chain 20 shown schematically in FIGS. 1 and 2 is formed.

The coupling elements consist of corresponding upper coupling elements 31A and 31B, and corresponding lower coupling elements 32A and 32B. The lower coupling element 32A consists of a nose-shaped shoulder on the holder 30 with a hole. On the opposite side, displaced upward, is the second lower coupling element 32B, which consists of a shoulder bearing a downwardly pointing pin, which can be pivotally inserted with play into the bore of the adjacent lower coupling element 32A.

The upper coupling element 31A corresponds essentially to the lower coupling element 32A, with the difference, however, that a longitudinal slit at the side leads into the hole. The second upper coupling element 31B has an upwardly pointing pin, which can be clicked resiliently into the hole of the upper coupling element 31A of the adjacent holder. Two holders 30 are therefore coupled together, as follows: First, the pin of a lower coupling element 32B is inserted into the corresponding hole of the adjacent lower coupling element 32A, after which the upwardly pointing pin of the upper coupling element 31B is clicked from the side into the hole of the adjacent upper coupling element 31A. Thus, a flexible chain is created, where a space remains between the adjacent holders, in which can engage the blades of the star-shaped wheels 16, 17 and 18 to convey the chain.

In order to differentiate between the front and back sides, the holder 30 has a vertical groove 33 in the area of its upper edge.

It is of particular importance that a front window 34 be introduced into the entrance window of the optical detector 13 (FIG. 7) so that, when a specimen pan is introduced from above into the holder 30, its lower end, with the specimen therein, remains visible through the front window 34, that is to say, that the luminescence reaction taking place thereat after injection of the activator, can be detected by the photocathode 13B of the photodetector 13.

Figure 7:
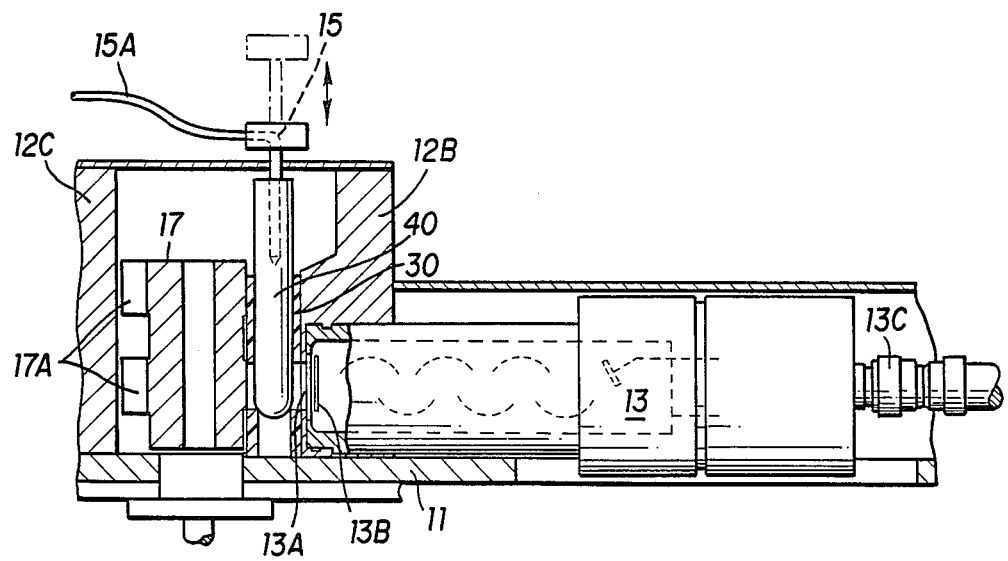
FIG. 7 is a cross-sectional view of the measuring station of the measuring instrument taken along the line A—A of FIG. 2.

As can likewise be seen in FIG. 7, the wall thickness of the holder 30 in its lower part is greater than in its upper part so that, with identical outside diameter, a smaller internal cross section is created in the lower part. Thus, a substantially annular bearing surface results for the hemispherical lower end of the specimen pan containing the specimen, so that a definite seat is created to ensure that the specimen is located in the window 34 during the luminescence measurement, and thus opposite the photocathode 13B.

A second window 35 is installed on the wall of the holder 30 opposite the front window 34, at the same level, so that this holder can also be used for turbidimetry, if a continuous light path is required instead of a luminescence measurement.

Figure 5:
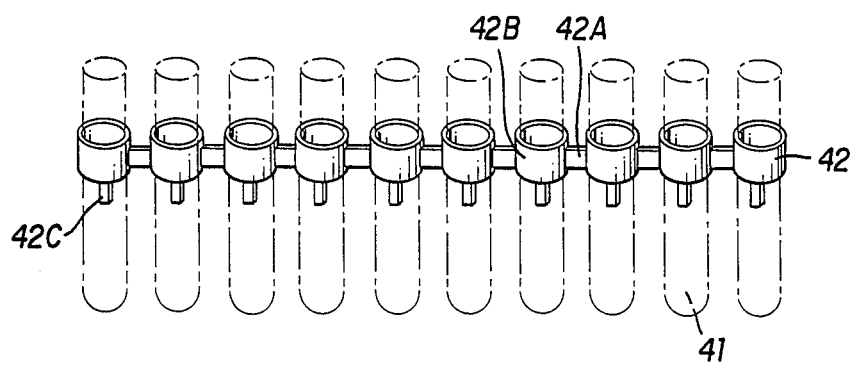
FIG. 5 is a perspective view of a second embodiment of a group of specimen pans, whose specimen pans are linked together by a coupling element.
Figure 6:
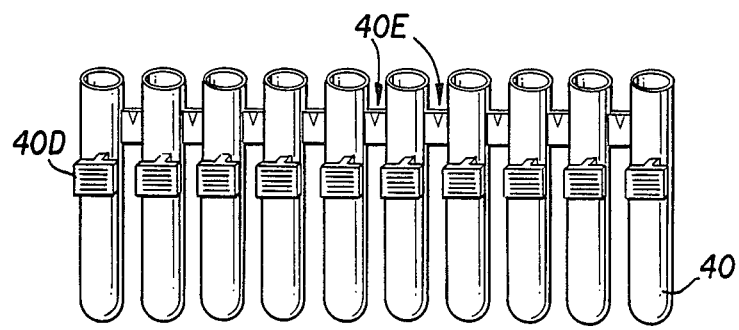
FIG. 6 is a perspective view of a construction of the first embodiment shown in FIG. 4.

Specimen pans, each with the specimen to be measured, are inserted from above into the specimen chain 20, which is made up of a rather large number of the holders 30 described earlier. These specimen pans are then seated, as described above, on the lower section of the holder 30. Owing to the scheme advocated in the present invention, which avoids removal and, thereby, isolation of the specimen pans from their holders 30 in the measuring station, an important, advantageous construction of the specimen pans results, as shown in FIGS. 4 to 6.

The fundamental idea is to combine several specimen pans 40 into one group of specimen pans, with the distance between axes of the individual specimen pans 40 corresponding to the distance between axes of the successively coupled holders 30, so that a group of specimen pans can together be inserted into the corresponding number of holders or removed therefrom. Advantageously, this occurs in the loading and unloading station 19B (FIG. 2), whose length corresponds to the length of a group of specimen pans.

Figure 4:
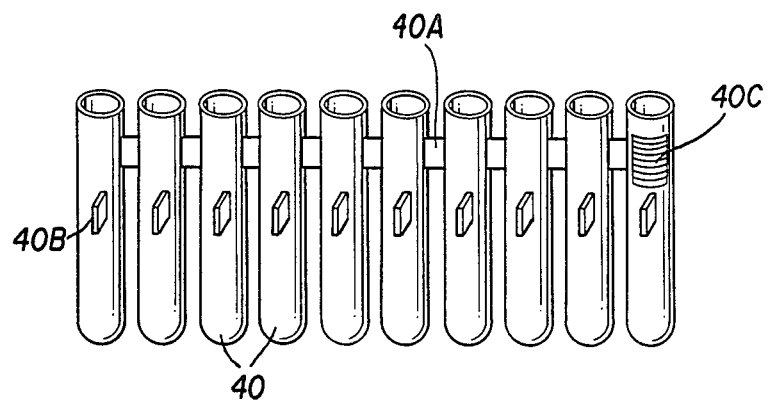
FIG. 4 shows a perspective view of a first embodiment of a group of specimen pans.

According to the first specific embodiment of a group of specimen pans shown in FIG. 4, ten specimen pans in the form of individual test tubes are joined together by flexible tie bars 40A. Each specimen pan 40 has a cam 40B on its front end.

When the group of specimen pans is inserted into the holders 30, this lateral cam 40B projects into the groove 33 (FIG. 3), thereby cancelling out the symmetry in the longitudinal axis of the group of specimens, thus permitting a clear definition of the sequence of the specimen pans and preventing interchanges during the allocation of the measured specimens.

On the same side as these cams 40B there are located on the specimen pans stickers 40C bearing a bar code for the individual identification of the particular specimen.

In another modification of this embodiment, provision is made (FIG. 6) that the cams 40B bear small signs 40D on their front side, onto which the bar code is applied.

According to another specific embodiment (FIG. 5), the specimen pans are not grouped as one piece into a group of specimens, but instead are joined together with a separate flexible coupling element 42 consisting essentially of rings 42B joined together by tie bars 42A. In this case, cams 42C are attached to the underside of the rings 42B. In this embodiment, commercial test tubes may be used, which are inserted in friction-lock fashion into rings 42B.

Vertical slots 40E may be provided in the connectors 40A, which enable them to be separated, so that the length of a group of specimens can be shortened as required.

The one-piece group of specimen pans shown in FIG. 4, or the coupling element 42 may be integrally formed of plastic material, such as polyethylene.

It is obvious that, when using the above-described groups of specimen pans joined flexibly together as shown in FIGS. 4-6, the radii of the guide elements and the cross sections of the guide channels must be so dimensioned that the specimen chain can pass without friction through the individual stations of the measuring instrument shown in FIGS. 1, 2 and 7. Therefore, depending on the construction of the groups of specimen pans and on the preparation required for each specimen, guideways may also be chosen which deviate from the guideways depicted by way of example in FIGS. 1 and 2. As an example, a linear guide channel may also be provided in the area of the point of measurement 19A, if additional pieces of apparatus are to be inserted therein.

We claim:

1. An instrument for measuring bioluminescence and chemiluminescence, comprising:
    a generally horizontal surface;
    a plurality of holders coupled to one another;
    a plurality of specimen pans in said holders;
    a front window formed in each holder;
    a guide means for guiding the movement of said holders on said surface, said guide means including a first guide channel having a lateral guide element, said lateral guide element having a generally semicircular surface at a measurement point;
    a drive means for driving said plurality of coupled holders through said guide means, said drive means including a central star-shaped wheel disposed within said semi-circular surface for driving said plurality of holders therebetween, wherein said star-shaped wheel includes radially extending blades which project into interstices between adjacent coupled holders for driving said holders along said guide channel; and
    an optical detector positioned at said point of measurement at a level corresponding with the front window of each holder and in a light-tight area for individually detecting bioluminescence or chemiluminescence in one of said specimen pans in one of the plurality of the coupled holders, wherein longitudinal axis of said optical detector is aligned with a bearing axis of said star-shaped wheel, and further wherein, when one of said specimen pans is at said measurement point, said blades of said star-shaped wheel provide a screen to screen out extraneous radiation from adjacent specimen pans and from an entrance or exit opening of said first guide channel.

2. The measuring instrument according to claim 1, wherein the holders (30) each have a second rear window (35) which is essentially diametrically opposed to the front window (34).

3. The measuring instrument according to claim 1, wherein a cover plate (14) covers the entire horizontal surface (11), sealing it off in light-tight fashion.

4. The measuring instrument according to any one of claims 3 and 1, wherein the guide channel includes two additional curved extensions which engage two additional star-shaped wheels (16, 18) one on each side of said first star-shaped wheel (17).

5. The measuring instrument according to claim 4, wherein said star-shaped wheels (16, 17, 18) are connected together via a drive chain and with a drive motor.

6. The measuring instrument according to claim 1, wherein said plurality of holders (30) have coupling elements on opposing sides, by which any desired number of holders can be connected together to pivot about a vertical axis thereby forming chain-members, and wherein said specimen pans are combined into one group of specimen pans, the distance between their axis corresponding to the distances between the axis of the holders (30), enabling said group of specimens being inserted into a corresponding sequence of holders (30).

7. The measuring instrument according to claim 6, wherein one group of specimen pans is made of one piece with flexible tie bars (40A).

8. The measuring instrument according to claim 6, wherein a separate, flexible coupling element (42) connects a plurality of specimen pans (40) into one group of specimen pans.

9. The measuring instrument according to claim 8, wherein the flexible coupling element is made up of ring-shaped elements (42B), which are connected to each other by one tie bar each (42A) and which can be plugged in or shifted over one specimen pan (40) each.

10. The measuring instrument according to claim 7 or 9, wherein the tie bars (40A, 42A) are comprised of a flexible material such that the group of specimen pans in the load-free state are linearly aligned without lateral stress by guide elements.

11. The measuring instrument according to claim 6, wherein guide means (12A, 12D) include at least one straight guide section as a loading and/or unloading station (19B) for said one group of specimen pans, and whose length corresponds at least to a length of said one group of specimen pans.

12. The measuring instrument according to claim 11, wherein at least one holder (30) has within a group of specimen pans a marker in the form of a groove (33) placed outside the longitudinal symmetry plane.

13. The measuring instrument according to claim 12, wherein all the holders (30) have a groove (33) and all the specimen pans (40, 41) have a cam (40B, 42B), which during insertion of the specimen pans (40, 41), engage in the holders (30).

14. The measuring instrument according to claim 6, wherein at least one specimen pan (40, 41) of a group of specimen pans has a lateral cam (40B, 42B) disposed thereon.

15. The measuring instrument according to claim 14, wherein all the specimen pans (40) have a lateral cam, to which is attached a label (40D), whose plane is substantially parallel to the direction of conveyance.

* * * * *